United States Patent [19]

Mitchell

[11] Patent Number: 4,631,057
[45] Date of Patent: Dec. 23, 1986

[54] SHIELDED NEEDLE

[75] Inventor: Charles B. Mitchell, Greenville, S.C.

[73] Assignees: Dolores A. Smith; Norma A. Sampson; Earl W. Sampson, all of Fullerton, Calif. ; a part interest to each

[21] Appl. No.: 809,277

[22] Filed: Dec. 17, 1985

[51] Int. Cl.[4] ............................................. A61M 5/32
[52] U.S. Cl. .................................................... 604/198
[58] Field of Search ................ 604/198, 192, 187, 197

[56]     References Cited
U.S. PATENT DOCUMENTS 2,571,653 10/1951 Bastien .
2,845,065  7/1958 Gabriel ................................. 604/198
3,780,734 12/1973 Wulff .
3,890,971  6/1975 Leeson et al. .
4,170,993 10/1979 Alvarez .
4,356,822 11/1982 Winstead-Hall ................ 604/192 X
4,373,526  2/1983 Kling ................................... 604/198
4,425,120  1/1984 Sampson et al. .

Primary Examiner—John D. Yasko
Attorney, Agent, or Firm—Gordon L. Peterson

[57]     ABSTRACT

An apparatus for injecting a substance into a human or animal comprising a body, a needle coupled to the body and terminating in a point and a needle guard mounted on the body for movement from a retracted position in which the guard does not shield the needle to an extended position in which the guard shields the needle. The needle guard can be releasably retained in the retracted position and locked in the extended position. Locking of the needle guard is accomplished by interlocking members carried by the needle guard and by a collar mounted on the body.

9 Claims, 7 Drawing Figures

U.S. Patent  Dec. 23, 1986  4,631,057
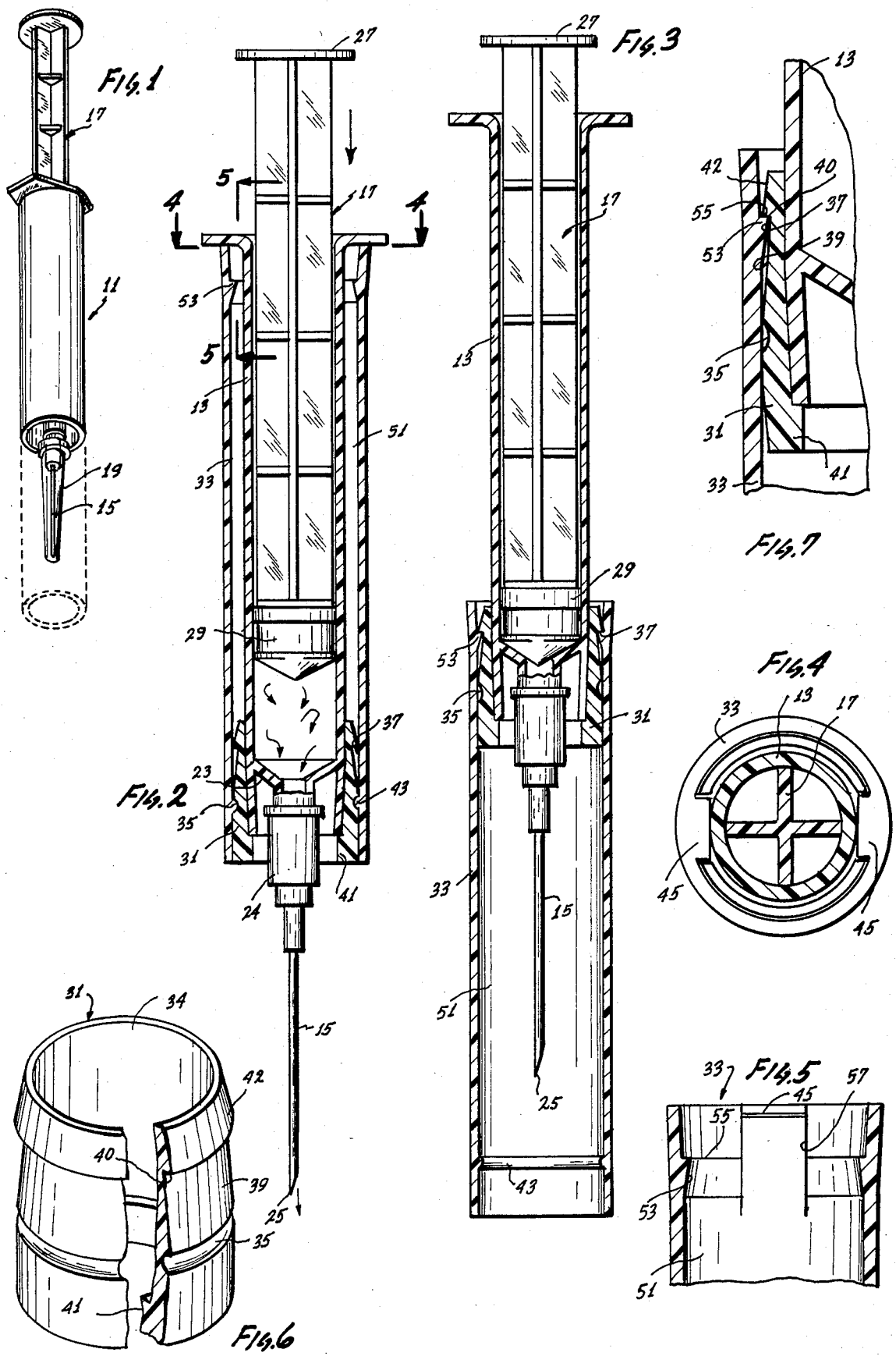

SHIELDED NEEDLE

BACKGROUND OF THE INVENTION

As is well known, a hypodermic syringe is used to inject substances into human and animal bodies. A typical hypodermic syringe comprises a barrel or body adapted to contain the substance to be injected, a hypodermic needle coupled to the barrel and means, such as a plunger, for forcing the substance from the barrel through the needle.

Hypodermic syringes, I.V. needles and the like are typically disposable and are discarded after use. One problem presented by the disposal of these devices is in shielding the sharp end of the needle so that those handling it will not be stuck. This is particularly important because, following the injection, the needle may be contaminated and spread disease, such as hepatitis and AIDS.

Typically, a hypodermic syringe is supplied with a tubular shield which is slipped over the needle from the pointed end and releasably retained on the syringe. One way to shield the needle following its use is to replace the tubular shield. Unfortunately, the passage into the shield is of small diameter and the shield must be inserted over the sharp end of the needle. Consequently, there is a substantial risk to the person attempting to do this, particularly if the reshielding is attempted during emergency periods or other times of high stress.

Other methods of needle shielding are known and are described, for example, in Bastien U.S. Pat. No. 2,571,653, Leeson et al U.S. Pat. No. 3,890,971 and Wulff U.S. Pat. No. 3,780,734. However, each of these devices suffers from various drawbacks. For example, the Bastien guarded syringe does not positively retain the guard in position, and the devices shown in the Leeson and Wulff patents are quite complex with the latter device being particularly adapted for animal usage.

Sampson et al Pat. No. 4,425,120 shows an effective way of shielding a needle. However, the device of the earlier patent requires rotational movement in order to lock the guard in the extended position. The shielded device of the later Sampson et al patent is also effective but is somewhat more complex to manufacture than is desired.

SUMMARY OF THE INVENTION

This invention provides a shielded needle apparatus which is of relatively simple construction and is easily manufactured. No modifications to the body of the injecting apparatus are required, and accordingly, the shielding features of this invention are readily adaptable to virtually any injecting apparatus, such as a hypodermic syringe, I.V. needle or the like. With this invention, only two components need to be added to a conventional injection apparatus in order to provide it with the shielding features of the invention.

According to this invention, the shielding features are provided by a collar carried by the body and a needle guard which is mounted on the body for movement relative to the body and over the collar from a retracted position in which the guard does not materially obstruct access to the point of the needle to an extended position in which the guard obstructs access to the point of the needle. The extended and retracted positions are spaced apart axially, and no rotation of the needle guard is required in moving between these positions. Means is provided for releasably retaining the needle guard in the retracted position. Also, interlocking means is provided on the needle guard and the collar, and the interlocking means is responsive to movement of the needle guard to the extended position to lock the needle guard in the extended position. Thus, by adding only a collar and the needle guard, a conventional injection apparatus can be provided with needle shielding features.

Although various different constructions are possible, the interlocking means preferably includes a groove in the collar and a projection carried by the needle guard. The projection is receivable in the groove to positively lock the needle guard in the extended position. The lock is positive in that the interlocking members are not simply held together by a biasing force or detent force which is readily overcome to allow movement of the needle guard. Rather, absent some unexpected or extraordinary force, the needle guard cannot be moved from the extended position. The projection preferably includes a shoulder and said needle guard and collar have cooperating inclined cam surfaces for facilitating the locking engagement of the shoulder and groove.

The needle guard slides over the collar in moving from the retracted position to the extended position, and the projection is also engageable with the body to reduce the relative radial movement or play between the needle guard and the body. The needle guard may have a plurality of teeth projecting generally radially inwardly to assist in guiding the needle guard in moving from the retracted position to the extended position.

Although the collar can be formed integrally with the body, preferably they are separate members, and the collar is attached to the body. To save material and to prevent the collar from prematurely restricting movement of the projection of the needle guard, the collar is preferably shorter than the needle guard and is located closely adjacent the distal end of the body. The projection carried by the needle guard is preferably closely adjacent the proximal end of the needle guard.

Although the needle guard can be releasably retained in the retracted position in different ways, preferably this is accomplished by cooperating means on the collar and the needle guard. Such cooperating means may take the form of interlocking means, and the interlocking means may include a groove on the collar and a projection on the needle guard. The projections carried by the guard for retaining the needle guard in the retracted position and for locking the needle guard in the extended position are preferably axially spaced.

The invention, together with additional features and advantages thereof, may best be understood by reference to the following description taken in connection with the accompanying illustrative drawing.

BRIEF DESCRIPTION OF THE DRAWING

FIG. 1 is an isometric view of a hypodermic syringe embodying one form of the shielded needle apparatus of this invention, with the needle guard in the retracted position in full lines and in the extended position in dashed lines.

FIG. 2 is a longitudinal sectional view through the apparatus with the needle guard in the retracted position.

FIG. 3 is a sectional view similar to FIG. 2, with the needle guard advanced axially to the extended position.

FIG. 4 is a sectional view taken generally along line 4—4 of FIG. 2.

FIG. 5 is an enlarged fragmentary, sectional view taken generally along line 5—5 of FIG. 2.

FIG. 6 is an isometric view, partially in section, of one form of collar.

FIG. 7 is an enlarged, fragmentary sectional view of interlocking regions of the collar and needle guard in the extended position.

DESCRIPTION OF THE PREFERRED EMBODIMENT

FIGS. 1-3 show an apparatus for injecting a substance into a human or animal in the form of a hypodermic syringe 11 which generally comprises a barrel or body 13 adapted to contain a substance to be injected, a hypodermic needle 15, a plunger 17 and a shield 19. The plunger 17 is mounted for axial sliding movement within the body 13 for forcing the substance from the body through the passage of the needle in a conventional manner.

The body 13, the needle 15, the plunger 17 and the shield 19 may be of conventional construction. Thus, the body 13, in the illustrated embodiment, is in the form of a hollow plastic cylinder having appropriate graduations or indicia (not shown) so that the amount of substance to be injected can be determined. The barrel 13 has an end wall 23 to which the needle 15 is attached in a conventional manner by a needle mounting member 24. The needle 15 is coaxial with the barrel 13 and terminates in a sharp point 25 at the distal end of the needle. The plunger 17 has a flat outer end 27 which facilitates manual movement of the plunger 17 within the barrel, and it has a piston 29 at its inner end to facilitate drawing a liquid into the body 13 or expelling the liquid from the body through the passage of the needle 15. The shield 19 is in the form of an elongated hollow cylinder which is frictionally retained on the needle mounting member 24.

The syringe 11 as described above is conventional, and the needle-shielding features of this invention are particularly adapted for use with a conventional syringe 11 of this type, as well as other substance-injecting apparati. With this invention, a collar 31 is attached to the body 13 at the distal end of the body, and a needle guard 33 is mounted on the body for movement relative to the body and over the collar from a retracted position in which the needle guard does not obstruct access to the point 25 of the needle (FIG. 2) to an extended position in which the needle guard substantially obstructs access to the point of the needle (FIG. 3).

Although various constructions are possible, the collar 31 in the embodiment illustrated is in the form of an axially short, generally cylindrical and tubular, molded plastic member which completely surrounds a distal region of the body 13 and which has a generally cylindrical axial passage 34 extending through it. The collar 31 has an outwardly opening, annular groove 35 in a central region of its outer surface and an annular groove 37 closely adjacent its proximal end. The groove 37 is formed by a conical surface 39 and an annular shoulder 40. The collar 31 is optionally provided with an annular flange 41 at its distal end which projects radially inwardly for engagement with the distal end of the body 13 as shown in FIGS. 2 and 3. The collar 31 has an exterior conical cam surface 42 which slopes radially outwardly as it extends distally and which terminates at the groove 37 to facilitate locking the needle guard 33 in the extended position.

The needle guard 33 in the embodiment illustrated is in the form of an elongated, generally cylindrical plastic sleeve. The needle guard 33 has an annular rib or projection 43 adjacent its distal end, and a pair of diametrically opposed, radially inwardly extending teeth 45 at its proximal end. The opposite ends of the needle guard 33 are open.

Although various constructions are possible, the needle guard 33 has a generally cylindrical passage 51 extending completely through it and a conical cam surface 53 (FIG. 5) near the proximal end of the needle guard. The conical cam surface 53 tapers slightly radially inwardly as it extends proximally and terminates in a projection which includes an annular shoulder 55 (FIG. 5) which is spaced slightly distally from the teeth 45. The conical cam surface 53 and the shoulder 55 may be interrupted by grooves 57 (only one being shown in FIG. 5) leading to each of the teeth 45.

To assemble the collar 31 and the needle guard 33, the needle guard may be placed on the collar as shown in FIG. 2 to form a subassembly, and the subassembly positioned over the body 13 also as shown in FIG. 2. The collar 31 is then attached to the body 13 as by sonic welding or an adhesive.

The syringe 11 may be shipped and stored with the needle guard 33 in the retracted position of FIG. 2 and with the shield 19 protecting the user from injury against the needle 15. In the retracted position, the rib 43 on the interior surface of the needle guard 33 is seated in the annular groove 35 of the collar 31. However, because of the rounded nature of the groove 35 and the rib 43 and because of the relatively shallow depth of the groove, the needle guard 33 is only releasably retained in the retracted position. In other words, it is relatively easy for the user to manually move the needle guard 33 from the retracted position to the extended position.

Prior to use, the shield 19 is removed, and the syringe 11 is used in the usual manner to withdraw medication from a drug vial and to inject that medication into a patient. Following this, the needle guard 33 is manually grasped and removed from the retracted position of FIG. 2 to the extended position of FIG. 3.

To reach the extended position, the user slides the needle guard 33 distally and forces the conical surface 53 over the conical surface 42 at the proximal end portion of the collar 31 and into the groove 37 (FIGS. 3 and 7). The conical surface 42 facilitates the movement of the conical surface 53 over the proximal end portion of the collar 31 so that the shoulder 55 may snap into the groove 37. During the axial sliding movement of the needle guard 33 from the retracted position toward the extended position, the teeth 45 slide along, or are in slightly spaced relationship with, the outer surface of the body 13 to thereby support the proximal end of the needle guard in its sliding movement along the body. The collar serves as a bearing to support regions of the needle guard 33 which are distal to the teeth 45 in the advancing movement of the needle guard toward the extended position. In other words, the teeth 45 and the outer surface of the body 13 form a proximal bearing, and the collar 31 and the surface of the passage 51 form a distal bearing for the needle guard 33.

The shoulders 40 and 55 are preferably flat and radially extending as shown in FIG. 3 so that retrograde movement of the needle guard 33 from the extended position back to the retracted position will not occur in normal disposal of the used syringe absent unexpected or unusual forces on the needle guard. Because the teeth 45 and the region of the needle guard 33 are relatively rigid, it is also extremely difficult to advance the needle guard proximally of the position shown in FIG. 3. However, if this should occur, the groove 35 serves as a safety groove or backup to catch the teeth 45 to prevent movement of the needle guard 33 completely off of the body 13.

Although an exemplary embodiment of the invention has been shown and described, many changes, modifications and substitutions may be made by one having ordinary skill in the art without necessarily departing from the spirit and scope of this invention.

I claim:

1. An apparatus for injecting a substance into a human or animal comprising:
   a body adapted to contain the substance to be injected;
   means for mounting a hypodermic needle on the body with the needle having a passage extending therethrough and terminating in a point whereby the substance can pass from the body to and through the passage of the needle;
   a collar carried by said body;
   a needle guard;
   the needle guard being mounted on the body for movement relative to said body and over said collar from a retracted position in which the needle guard does not materially obstruct access to the point of the needle and an extended position in which the needle guard obstructs access to the point of the needle, said extended and retracted positions being axially spaced;
   means for releasably retaining the needle guard in the retracted position; and
   interlocking means on the needle guard and the collar responsive to movement of the needle guard to the extended position to lock the needle guard in the extended position.

2. An apparatus as defined in claim 1 wherein said interlocking means includes a groove in the collar and a projection carried by the needle guard.

3. An apparatus as defined in claim 2 wherein said projection includes a shoulder and said needle guard and collar have cooperating inclined cam surfaces for facilitating locking engagement of the shoulder in the groove.

4. An apparatus as defined in claim 2 including a plurality of teeth on the needle guard and projecting generally radially inwardly to assist in guiding the needle guard in moving from the retracted position to the extended position.

5. An apparatus as defined in claim 1 wherein said collar and body are separate members and the collar is attached to the body.

6. An apparatus as defined in claim 1 wherein the collar is shorter than the needle guard and closely adjacent the distal end of the body and the portion of the interlocking means on the needle guard is closely adjacent the proximal end of the needle guard.

7. An apparatus as defined in claim 1 wherein the retaining means includes second interlocking means on the needle guard and collar for releasably retaining the needle guard in the retracted position.

8. An apparatus as defined in claim 1 wherein the interlocking means includes a first projection on the needle guard and a first recess on the collar and the retaining means includes second interlocking means on the needle guard and collar for releasably retaining the needle guard in the retracted position and the portion of the second interlocking means on the needle guard is spaced distally of the first projection.

9. An apparatus as defined in claim 1 including a removable shield covering said needle and plunger means movable into said body for forcing the substance from the body through the passage of the needle.

* * * * *